(12) United States Patent
Beraud et al.

(10) Patent No.: US 6,294,371 B1
(45) Date of Patent: Sep. 25, 2001

(54) MOTOR PROTEINS AND METHODS FOR THEIR USE

(75) Inventors: Christophe Beraud, San Francisco; Richard Freedman, San Mateo, both of CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 09/621,233

(22) Filed: Jul. 21, 2000

(51) Int. Cl.[7] .............................. C12N 1/20; C12N 15/00; C12N 15/09; C12N 15/63; C12N 15/70; C12N 15/74; C12N 15/55; C12N 9/18; C07H 21/04

(52) U.S. Cl. .................. 435/252.3; 536/23.2; 435/320.1; 435/196

(58) Field of Search ........................ 536/23.2; 435/320.1, 435/252.3, 196

(56) References Cited

PUBLICATIONS

Pereira et al. (2000) "Mitochondrial association of a plus end–directed microtubule motor expressed during mitosis in Drosophila" J. Cell Biol. 136:1081–1090.
Wood et al. (1997) Genbank Accession #Z97211. Direct Submission, S. pombe chromosome II cosmid c2F12.
Purnelle et al. (1998) Genbank Accession #AL023587. Direct Submission, S. pombe chromosome II cosmid c649.
Rieger et al. (1996) Genbank Accession #Z72739; Y3135. Direct Submission, S. cerevisiae chromosome VII.
Stewart et al. (1997) Genbank Accession #U89264. Direct Submission, Dm Kinesin–like protein 67a.

*Primary Examiner*—Rebecca E. Prouty
*Assistant Examiner*—David J. Steadman
(74) *Attorney, Agent, or Firm*—Lauren L. Stevens; Beyer Weaver & Thomas LLP

(57) ABSTRACT

The invention provides isolated nucleic acid and amino acid sequences of HsKip3b, antibodies to HsKip3b, methods of screening for HsKip3b modulators using biologically active HsKip3b, and kits for screening for HsKip3b modulators.

6 Claims, 2 Drawing Sheets

FIG. 1

```
  1  GTGACCGTGG GCCTCCCTCT GGGGACCTTG CAGATGGTGG TTCTCATGGA
 51  CCCAATGGAG GATCCCGACG ACATCCTGCG GGCGCATCGC TCCCGGGAGA
101  AGTCCTACCT GTTCGACGTG GCCTTTGACT TCACCGCCAC CCAGGAGATG
151  GTGTATCAGG CCACCACCAA GAGCCTCATC GAGGGCGTCA TCTCAGGCTA
201  CAATGCCACT GTCTTTGCCT ATGGCCCCAC AGGCTGTGGG AAAACCTACA
251  CCATGCTGGG CACAGACCAG GAGCCTGGCA TCTATGTTCA GACCCTCAAC
301  GACCTCTTCC GTGCCATCGA GGAGACCAGC AATGACATGG AGTATGAGGT
351  CTCCATGTCC TACCTGGAGA TCTACAATGA GATGATCCGG GACCTGCTGA
401  ACCCCTCCCT GGGCTACCTG GAGCTGCGGG AGGACTCTAA GGGGGTGATC
451  CAGGTGGCCG GCATCACCGA ANNNNNNNNN NNNNNNNNNN NNNNNATCAT
501  GCAGCTGCTG ATGAAGGGGA ACCGGCAGAG GACCCAGGAG CCCACGGCCG
551  CCAACCAGAC GTCCTCCCGC TCCACGCGG GCCGCCTGTT CATGATCGAC
601  CTGGCTGGCT CAGAGCGCGC CTCGCAGACA CAGAATCGTG GCAGCGTAT
651  GAAGGAGGGG GCCCACATCA ACCGCTCACT GCTGGCACTG GCAACTGCA
701  TCAACGCCCT GAGCGACAAG GGTAGCAACA AGTACATCAA CTATCGCGAC
751  AGCAAGCTCA CCCGGCTCCT GAAGGACTCT CTGGGAGGAA ACAGCCGCAC
801  AGTGATGATC GCTCACATCA GTCCTGCGAG CAGTGCCTTC GAGGAGTCCC
851  GGAACACCCT GACCTACGCC GGCCGGGCCA AGAACATTAA GACTAGG
```

FIG. 2

```
  1  VTVGLPLGTL QMVVLMDPME DPDDILRAHR SREKSYLFDV AFDFTATQEM

51  VYQATTKSLI EGVISGYNAT VFAYGPTGCG KTYTMLGTDQ EPGIYVQTLN

101  DLFRAIEETS NDMEYEVSMS YLEIYNEMIR DLLNPSLGYL ELREDSKGVI

151  QVAGITEXXX XXXXXIMQLL MKGNRQRTQE PTAANQTSSR SHAGRLFMID

201  LAGSERASQT QNRGQRMKEG AHINRSLLAL GNCINALSDK GSNKYINYRD

251  SKLTRLLKDS LGGNSRTVMI AHISPASSAF EESRNTLTYA GRAKNIKTR
```

MOTOR PROTEINS AND METHODS FOR THEIR USE

FIELD OF THE INVENTION

The invention provides isolated nucleic acid and amino acid sequences of HsKip3b, methods of detecting HsKip3b and screening for HsKip3b modulators using biologically active HsKip3b, and kits for screening for HsKip3b modulators.

BACKGROUND OF THE INVENTION

The kinesin superfamily is an extended family of related microtubule motor proteins. It can be classified into at least 8 subfamilies based on primary amino acid sequence, domain structure, velocity of movement, and cellular function. This family is exemplified by "true" kinesin, which was first isolated from the axoplasm of squid, where it is believed to play a role in anterograde axonal transport of vesicles and organelles (see, e.g., Goldstein, *Annu. Rev. Genet.* 27:319–351 (1993)). Kinesin uses ATP to generate force and directional movement associated with microtubules.

Within this functional group of kinesins resides a group of kinesins from several organisms that share significant sequence homology. These include Drosophila Klp67A, *S. pombe* BC2F12.1, *S. pombe* BC649.01, *S. cerevisiae* Kip3, HsKif3a, and CeLF22F4.3.

Drosophila Klp67A has been shown to be a plus end-directed motor. This activity implicates KPL67A in the localization of micochondria in undifferentiated cell types. In situ hybridization studies of the KLP67A MRNA during embryogenesis and larval central nervous system development indicate a proliferation-specific expression pattern. When affinity-purified anti-KLP67A antisera are used to stain blastoderm embryos, mitochondria in the region of the spindle asters are labeled. These data suggest that KLP67A is a mitotic motor with the role of positioning mitochondria near the spindle.

The discovery of a new kinesin motor protein, and more particularly, one having sequence homology to KLP67A, and the polynucleotides encoding it satisfies a need in the art by providing new compositions which are useful in the diagnosis, prevention, and treatment of cancer, neurological disorders, and disorders of vesicular transport.

SUMMARY OF THE INVENTION

The present invention is based on the discovery of a new human kinesin motor protein, HsKip3b, the polynucleotide encoding HsKip3b, and the use of these compositions for the diagnosis, treatment, or prevention of cancer, neurological disorders, and disorders of vesicular transport.

In one aspect, the invention provides an isolated nucleic acid sequence encoding a kinesin superfamily motor protein, wherein the motor protein has the following properties: (i) the protein's activity includes microtubule stimulated ATPase activity; and (ii) the protein has a sequence that has greater than 70% amino acid sequence identity to SEQ ID NO:2 as measured using a sequence comparison algorithm. In one embodiment, the protein further specifically binds to polyclonal antibodies raised against SEQ ID NO:2.

In one embodiment, the nucleic acid encodes HsKip3b or a fragment thereof. In another embodiment, the nucleic acid encodes SEQ ID NO:2. In another embodiment, the nucleic acid has a nucleotide sequence of SEQ ID NO:1.

In one aspect, the nucleic acid comprises a sequence which encodes an amino acid sequence which has greater than 70% sequence identity with SEQ ID NO:2, preferably greater than 80%, more preferably greater than 90%, more preferably greater than 95% or, in another embodiment, has 98 to 100% sequence identity with SEQ ID NO:2.

In one embodiment, the nucleic acid comprises a sequence which has greater than 55 or 60% sequence identity with SEQ ID NO:1, preferably greater than 70%, more preferably greater than 80%, more preferably greater than 90 or 95% or, in another embodiment, has 98 to 100% sequence identity with SEQ ID NO:1. In another embodiment provided herein, the nucleic acid hybridizes under stringent conditions to a nucleic acid having a sequence or complementary sequence of SEQ ID NO:1.

In another aspect, the invention provides an expression vector comprising a nucleic acid encoding a kinesin superfamily motor protein, wherein the motor protein has the following properties: (i) the protein's activity includes microtubule stimulated ATPase activity; and (ii) the protein has a sequence that has greater than 70% amino acid sequence identity to SEQ ID NO:2 as measured using a sequence comparison algorithm. The invention further provides a host cell transfected with the vector.

In another aspect, the invention provides an isolated kinesin superfamily motor protein, wherein the protein has one or more of the properties described above. In one embodiment, the protein specifically binds to polyclonal antibodies generated against a motor domain, tail domain or other fragment of HsKip3b. In another embodiment, the protein comprises an amino acid sequence of SEQ ID NO:2.

In one aspect, the protein provided herein comprises an amino acid sequence which has greater than 70% sequence identity with SEQ ID NO:2, preferably greater than 80%, more preferably greater than 90%, more preferably greater than 95% or, in another embodiment, has 98 to 100% sequence identity with SEQ ID NO:2.

The invention features a substantially purified polypeptide comprising the amino acid sequence of SEQ ID NO:2 or a fragment thereof and more particularly, the motor domain of the amino acid sequence of SEQ ID NO:2 or a fragment thereof.

In one embodiment, the present invention provides a method of identifying a candidate agent as a modulator of the activity of a target protein. The method comprises adding a candidate agent to a mixture comprising a target protein which directly or indirectly produces ADP or phosphate, under conditions that normally allow the production of ADP or phosphate. The method further comprises subjecting the mixture to a reaction that uses said ADP or phosphate as a substrate under conditions that normally allow the ADP or phosphate to be utilized and determining the level of activity of the reaction as a measure of the concentration of ADP or phosphate. A change in the level between the presence and absence of the candidate agent indicates a modulator of the target protein.

The phrase "use ADP or phosphate" means that the ADP or phosphate are directly acted upon by detection reagents. In one case, the ADP, for example, can be hydrolyzed or can be phosphorylated. As another example, the phosphate can be added to another compound. As used herein, in each of these cases, ADP or phosphate is acting as a substrate.

Preferably, the target protein either directly or indirectly produces ADP or phosphate and comprises a motor domain. More preferably, the target protein comprises a kinesin superfamily motor protein as described above and most preferably, the target protein comprises HsKip3b or a fragment thereof Also provided are modulators of the target protein including agents for the treatment of cellular proliferation, including cancer, hyperplasias, restenosis, cardiac hypertrophy, immune disorders and inflammation. The agents and compositions provided herein can be used in variety of applications which include the formulation of sprays, powders, and other compositions. Also provided herein are methods of treating cellular proliferation disorders such as cancer, hyperplasias, restenosis, cardiac hypertrophy, immune disorders and inflammation, for treating disorders associated with HsKip3b activity, and for inhibiting HsKip3b.

BRIEF DESCRIPTION OF THE DRAWINGS

FIG. 1 shows an embodiment of a nucleic acid sequence encoding a particularly preferred fragment of the motor domain of HsKip3b (SEQ ID NO:1).

FIG. 2 shows the amino acid sequence of a particularly preferred fragment of the motor domain of HsKip3b (SEQ ID NO:2).

DETAILED DESCRIPTION OF THE INVENTION

I. Definitions

"ADP" refers to adenosine diphosphate and also includes ADP analogs, including, but not limited to, deoxyadenosine diphosphate (dADP) and adenosine analogs. "Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. The term antibody also includes antibody fragments either produced by the modification of whole antibodies or those synthesized de novo using recombinant DNA methodologies.

An "anti-HsKip3b" antibody is an antibody or antibody fragment that specifically binds a polypeptide encoded by the HsKip3b gene, cDNA, or a subsequence thereof.

"Biologically active" target protein refers to a target protein that has one or more of kinesin protein's biological activities, including, but not limited to microtubule stimulated ATPase activity, as tested, e.g., in an ATPase assay. Biological activity can also be demonstrated in a microtubule gliding assay or a microtubule binding assay. "ATPase activity" refers to ability to hydrolyze ATP. Other activities include polymerization/depolymerization (effects on microtubule dynamics), binding to other proteins of the spindle, binding to proteins involved in cell-cycle control, or serving as a substrate to other enzymes, such as kinases or proteases and specific kinesin cellular activities, such as chromosome congregation, axonal transport, etc.

"Biological sample" as used herein is a sample of biological tissue or fluid that contains a target protein or a fragment thereof or nucleic acid encoding a target protein or a fragment thereof. Biological samples may also include sections of tissues such as frozen sections taken for histological purposes. A biological sample comprises at least one cell, preferably plant or vertebrate. Embodiments include cells obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

A "comparison window" includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the global alignment algorithm of Needleman & Wunsch, J. Mol. Biol. 48:443 (1970), by the search for similarity methods of Pearson & Lipman, Proc. Natl. Acad. Sci. USA 85:2444 (1988) and Altschul et al. Nucleic Acids Res. 25(17): 3389–3402 (1997), by computerized implementations of these algorithms (GAP, BESTFIT, FASTA, and BLAST in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments. It can also plot a dendrogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). As a general rule, PileUp can align up to 500 sequences, with any single sequence in the final alignment restricted to a maximum length of 7,000 characters.

The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. A series of such pairwise alignments that includes increasingly dissimilar sequences and clusters of sequences at each iteration produces the final alignment.

"Variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCT all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each degenerate codon in a nucleic acid can be modified to yield a functionally identical molecule. Accordingly, each silent variation of a nucleic acid which encodes a polypeptide is implicit in each described sequence.

Also included within the definition of target proteins of the present invention are amino acid sequence variants of wild-type target proteins. These variants fall into one or more of three classes: substitutional, insertional or deletional variants. These variants ordinarily are prepared by site specific mutagenesis of nucleotides in the DNA encoding the target protein, using cassette or PCR mutagenesis or other techniques well known in the art, to produce DNA encoding the variant, and thereafter expressing the DNA in recombinant cell culture. Variant target protein fragments having up to about 100–150 amino acid residues may be prepared by in vitro synthesis using established techniques. Amino acid sequence variants are characterized by the predetermined nature of the variation, a feature that sets them apart from naturally occurring allelic or interspecies variation of the target protein amino acid sequence. The variants typically exhibit the same qualitative biological activity as the naturally occurring analogue, although variants can also be selected which have modified characteristics.

Amino acid substitutions are typically of single residues; insertions usually will be on the order of from about 1 to about 20 amino acids, although considerably longer insertions may be tolerated. Deletions range from about 1 to about 20 residues, although in some cases, deletions may be much longer.

Substitutions, deletions, and insertions or any combinations thereof may be used to arrive at a final derivative. Generally, these changes are done on a few amino acids to minimize the alteration of the molecule. However, larger characteristics may be tolerated in certain circumstances.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, Proteins (1984)).

"Cytoskeletal component" denotes any molecule that is found in association with the cellular cytoskeleton, that plays a role in maintaining or regulating the structural integrity of the cytoskeleton, or that mediates or regulates motile events mediated by the cytoskeleton. Includes cytoskeletal polymers (e.g., actin filaments, microtubules, intermediate filaments, myosin fragments), molecular motors (e.g., kinesins, myosins, dyneins), cytoskeleton associated regulatory proteins (e.g., tropomysin, alpha-actinin) and cytoskeletal associated binding proteins (e.g., microtubules associated proteins, actin binding proteins).

"Cytoskeletal function" refers to biological roles of the cytoskeleton, including but not limited to the providing of structural organization (e.g., microvilli, mitotic spindle) and the mediation of motile events within the cell (e.g., muscle contraction, mitotic chromosome movements, contractile ring formation and function, pseudopodal movement, active cell surface deformations, vesicle formation and translocation.)

A "diagnostic" as used herein is a compound, method, system, or device that assists in the identification and characterization of a health or disease state. The diagnostic can be used in standard assays as is known in the art.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"High stringency conditions" may be identified by those that: (1) employ low ionic strength and high temperature for washing, for example 0.015M sodium chloride/0.0015 M sodium citrate/0.1% sodium dodecyl sulfate at 50° C.; (2) employ during hybridization a denaturing agent such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"High throughput screening" as used herein refers to an assay which provides for multiple candidate agents or samples to be screened simultaneously. As further described below, examples of such assays may include the use of microtiter plates which are especially convenient because a large number of assays can be carried out simultaneously, using small amounts of reagents and samples.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, or plant cells. Both primary cells and cultured cell lines are included in this definition.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. Typically, stringent conditions will be those in which the salt concentration is less than about 1.0M sodium ion, typically about 0.05 to 1.0M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The terms "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. Preferably, the percent identity exists over a region of the sequence that is at least about 25 amino acids in length, more preferably over a region that is 50 or 100 amino acids in length. This definition also refers to the complement of a test sequence, provided that the test sequence has a designated or substantial identity to a reference sequence.

Preferably, the percent identity exists over a region of the sequence that is at least about 25 nucleotides in length, more preferably over a region that is 50 or 100 nucleotides in length.

When percentage of sequence identity is used in reference to proteins or peptides, it is recognized that residue positions that are not identical often differ by conservative amino acid substitutions, where amino acid residues are substituted for other amino acid residues with similar chemical properties (e.g,. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. The scoring of conservative substitutions can be calculated according to, e.g., the algorithm of Meyers & Millers, Computer Applic.

Biol. Sci. 4:11–17 (1988), e.g., as implemented in the program PC/GENE (Intelligenetics, Mountain View, Calif.).

The terms "isolated", "purified", or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In an isolated gene, the nucleic acid of interest is separated from open reading frames which flank the gene of interest and encode proteins other than the protein of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

A "label" is a composition detectable by spectroscopic, photochemical, biochemical, immunochemical, or chemical means. For example, useful labels include fluorescent proteins such as green, yellow, red or blue fluorescent proteins, radioisotopes such as $^{32}p$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radiolabel into the peptide, and used to detect antibodies specifically reactive with the peptide).

A "labeled nucleic acid probe or oligonucleotide" is one that is bound, either covalently, through a linker, or through ionic, van der Waals, or hydrogen bonds to a label such that the presence of the probe may be detected by detecting the presence of the label bound to the probe.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 µg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

"Modulators," "inhibitors," and "activators of a target protein" refer to modulatory molecules identified using in vitro and in vivo assays for target protein activity. Such assays include ATPase activity, microtubule gliding, microtubule depolarizing activity, and binding activity such as microtubule binding activity or binding of nucleotide analogs. Samples or assays that are treated with a candidate agent at a test and control concentration. The control concentration can be zero. If there is a change in target protein activity between the two concentrations, this change indicates the identification of a modulator. A change in activity, which can be an increase or decrease, is preferably a change of at least 20% to 50%, more preferably by at least 50% to 75%, more preferably at least 75% to 100%, and more preferably 150% to 200%, and most preferably is a change of at least 2 to 10 fold compared to a control. Additionally, a change can be indicated by a change in binding specificity or substrate.

"Molecular motor" refers to a molecule that utilizes chemical energy to generate mechanical force. According to one embodiment, the molecular motor drives the motile properties of the cytoskeleton.

The phrase "motor domain" refers to the domain of a target protein that confers membership in the kinesin superfamily of motor proteins through a sequence identity of approximately 35–45% identity to the motor domain of true kinesin.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. For example, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260)2605–2608 (1985); Cassol et al. 1992; Rossolini et al. Mol. Cell. Probes 8:91–98 (1994)). The term nucleic acid is used interchangeably with gene, cDNA, and mRNA encoded by a gene.

"Nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases. In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled with isotopes, chromophores, lumiphores, chromogens, or indirectly labeled such as with biotin to which a streptavidine complex may later bind. By assaying for the presence or absence of the probe, one can detect the presence or absence of the select sequence or subsequence.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. A target protein comprises a polypeptide demonstrated to have at least microtubule stimulated ATPase activity. Amino acids may be referred to herein by either their commonly known three letter symbols or by Nomenclature Commission. Nucleotides, likewise, may be referred to by their commonly accepted single-letter codes, i.e., the one-letter symbols recommended by the IUPAC-IUB.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA box element. A promoter also optionally includes distal enhancer or repressor elements which can be located as much as several thousand base pairs from the start site of transcription. A "constitutive" promoter is a promoter that is active under most environmental and developmental conditions. An "inducible" promoter is a promoter that is under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, antibodies raised to HsKip3b with the amino acid sequence encoded in SEQ ID NO:2 can be selected to obtain only those antibodies that are specifically immunoreactive with HsKip3b and not with other proteins, except for polymorphic variants, orthologs, alleles, and closely related homologues of HsKip3b. This selection may be achieved by subtracting out antibodies that cross react with molecules, for example, such as C. elegans unc-104 and human Kif1A. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to selectively (or specifically) bind to a protein, as defined above.

"Test composition" (used interchangeably herein with "candidate agent" and "test compound" and "test agent") refers to a molecule or composition whose effect on the interaction between one or more cytoskeletal components it is desired to assay. The "test composition" can be any molecule or mixture of molecules, optionally in a carrier.

A "therapeutic" as used herein refers to a compound which is believed to be capable of modulating the cytoskeletal system in vivo which can have application in both human and animal disease. Modulation of the cytoskeletal system would be desirable in a number of conditions including, but not limited to: abnormal stimulation of endothelial cells (e.g., atherosclerosis), solid and hematopoetic tumors and tumor metastasis, benign tumors, for example, hemangiomas, acoustic neuromas, neurofibromas, pyogenic granulomas, vascular malfunctions, abnormal wound healing, inflammatory and immune disorders such as rheumatoid arthritis, Bechet's disease, gout or gouty arritis, abnormal angiogenesis accompanying: rheumatoid arthritis, psoriasis, diabetic retinopathy, and other ocular angiogenic disease such as, macular degeneration, corneal graft rejection, corneal overgrowth, glaucoma, and Osler Webber syndrome.

II. The Target Protein

The present invention provides for the first time a nucleic acid encoding HsKip3b. This protein is a member of the kinesin superfamily of motor proteins. More specifically, the HsKip3b sequence of FIG. 2 shares approximately 50% identity with various members of the Kip3 family described above, including DmKlp67A (48%) and being closest in sequence to CeLF22F4.3 (58% identity).

In one aspect, HsKip3b can be defined by having at least one or preferably more than one of the following functional and structural characteristics. Functionally, HsKip3b will have microtubule-stimulated ATPase activity, and microtubule motor activity that is ATP dependent. HsKip3b activity can also be described in terms of its ability to bind microtubules.

The novel nucleotides sequences provided herein encode HsKip3b or fragments thereof. Thus, in one aspect, the nucleic acids provided herein are defined by the novel proteins provided herein. The protein provided herein comprises an amino acid sequence which has one or more of the following characteristics: greater than 70% sequence identity with SEQ ID NO:2, preferably greater than 80%, more preferably greater than 90%, more preferably greater than 95% or, in another embodiment, has 98 to 100% sequence identity with SEQ ID NO:2. As described above, when describing the nucleotide in terms of SEQ ID NO:1, the sequence identity may be slightly lower due to the degeneracy in the genetic code. Also included within the definition of the target proteins are amino acid sequence variants of wild-type target proteins.

Portions of the HsKip3b nucleotide sequence may be used to identify polymorphic variants, orthologs, alleles, and homologues of HsKip3b. This identification can be made in vitro, e.g., under stringent hybridization conditions and sequencing, or by using the sequence information in a computer system for comparison with other nucleotide sequences. Sequence comparison can be performed using any of the sequence comparison algorithms discussed below, with PILEUP as a preferred algorithm.

As will be appreciated by those in the art, the target proteins can be made in a variety of ways, including both synthesis de novo and by expressing a nucleic acid encoding the protein.

Target proteins of the present invention may also be modified in a way to form chimeric molecules comprising a fusion of a target protein with a tag polypeptide which provides an epitope to which an anti-tag antibody can selectively bind. The epitope tag is generally placed at the amino or carboxyl terminus of the target protein. Provision of the epitope tag enables the target protein to be readily detected, as well as readily purified by affinity purification. Various tag epitopes are well known in the art. Examples include poly-histidine (poly-his) or poly-histidine-glycine (poly-his-gly) tags; the flu HA tag polypeptide and its antibody 12CA5 (see, Field et al. (1988) Mol. Cell. Biol. 8:2159); the c-myc tag and the 8F9, 3C7, 6E10, G4, B7 and 9E10 antibodies thereto (see, Evans et a (1985) Molecular and Cellular Biology, 5:3610); and the Herpes Simplex virus glycoprotein D (gD) tag and its antibody (see, Paborsky et al., (1990) Protein Engineering, 3:547). Other tag polypeptides include the Flag-peptide (see, Hopp et al. (1988) BioTechnology 6:1204); the KT3 epitope peptide (see, Martine et al. (1992) Science, 255:192); tubulin epitope peptide (see, Skinner (1991) J. Biol. Chem. 266:15173); and the T7 gene 10 protein peptide tag (see, Lutz-Freyermuth et al. (1990) Proc. Natl. Acad. Sci. USA 87:6393.

The biological activity of any of the peptides provided herein can be routinely confirmed by the assays provided herein such as those which assay ATPase activity or microtubule binding activity. In one embodiment, polymorphic variants, alleles, and orthologs, homologues of HsKip3b are confirmed by using a ATPase or microtubule binding assays as known in the art.

The isolation of biologically active HsKip3b for the first time provides a means for assaying for modulators of this kinesin superfamily protein. Biologically active HsKip3b is useful for identifying modulators of HsKip3b or fragments thereof and kinesin superfamily members using in vitro assays such as microtubule gliding assays, ATPase assays (Kodama et al., *J. Biochem.* 99:1465–1472 (1986); Stewart et al, *Proc. Nat'l Acad. Sci. USA* 90:5209–5213 (1993)), and binding assays including microtubule binding assays (Vale et al., *Cell* 42:39–50 (1985)). In vivo assays and uses are provided herein as well. Also provided herein are methods of identifying candidate agents which bind to HsKip3b and portions thereof.

As further described herein, a wide variety of assays, therapeutic and diagnostic methods are provided herein which utilize the novel compounds described herein. The uses and methods provided herein, as further described below have in vivo, in situ, and in vitro applications, and can be used in medicinal, veterinary, agricultural and research based applications.

III. Isolation of the Gene Encoding HsKip3b

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from mass spectroscopy, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter etal., *Nucleic Acids Res.* 12:6159–6168 (1984). Purification of oligonculeotides is by either native acrylamide gel electrophoresis or by anion exchange HPLC as described in Pearson & Reanier, *J. Chrom.* 225:137–149 (1983).

The sequence of the cloned genes and synthetic oligonucleotides can be verified after cloning using, e.g., the chain termination method for sequencing double-stranded templates of Wallace et al, *Gene* 16:21–26 (1981).

B. Cloning Methods for the Isolation of Nucleotide Sequences Encoding HsKip3b

In general, the nucleic acid sequences encoding HsKip3b and related nucleic acid sequence homologs are cloned from cDNA and genomic DNA libraries or isolated using amplification techniques with oligonucleotide primers. Alternatively, expression libraries can be used to clone HsKip3b and HsKip3b homologues by detected expressed homologues immunologically with antisera or purified antibodies made against HsKip3b that also recognize and selectively bind to the HsKip3b homologue. Finally, amplification techniques using primers can be used to amplify and isolate HsKip3b from DNA or RNA. Amplification techniques using degenerate primers can also be used to amplify and isolate HsKip3b homologues. Amplification techniques using primers can also be used to isolate a nucleic acid encoding HsKip3b. These primers can be used, e.g., to amplify a probe of several hundred nucleotides, which is then used to screen a library for full-length HsKip3b.

Appropriate primers and probes for identifying the gene encoding homologues of HsKip3b in other species are generated from comparisons of the sequences provided herein. As described above, antibodies can be used to identify HsKip3b homologues.

For example, antibodies made to the motor domain of HsKip3b or to the whole protein are useful for identifying HsKip3b homlogues.

To make a cDNA library, one should choose a source that is rich in the mRNA of choice, e.g., HsKip3b. The mRNA is then made into cDNA using reverse transcriptase, ligated into a recombinant vector, and introduced into a recombinant host for propagation, screening and cloning. Methods for making and screening cDNA libraries are well known (see, e.g., Gubler & Hoffinan, Gene 25:263–269); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, Science 196:18–182 (1977). Colony hybridization is read out as generally described in Grunstein et al., Proc. Natl. Acad. Sci. USA, 72:3961–3965 (1975).

An alternative method of isolating HsKip3b nucleic acid and its homologues combines the use of synthetic oligonucleotide primers and amplification of an RNA or DNA template (see U.S. Pat. Nos. 4,683,195 and 4,683,202; PCR Protocols: A guide to Methods and Applications (Irnis et al., eds. 1990)). Methods such as polymerase chain reaction and ligase chain reaction can be used to amplify nucleic acid sequences of HsKip3b directly from mRNA, from cDNA, from genomic libraries or cDNA libraries. Degenerate oligonucleotides can be designed to amplify HsKip3b homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of HsKip3b encoding mRNA in physiological samples, for nucleic sequencing or for other purposes.

Genes amplified by the PCR reaction can be purified from agarose gels and cloned into an appropriate vector.

Gene expression of HsKip3b can also be analyzed by techniques known in the art, e.g., reverse transcription and amplification of mRNA, isolation of total RNA or poly A+RNA, northern blotting, dot blotting, in situ hybridization, RNase protection, quantitative PCR, and the like.

Synthetic oligonucleotides can be used to construct recombinant HsKip3b genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the HsKip3b gene. The specific subsequence is then ligated into an expression vector.

The gene for HsKip3b is typically cloned into intermediate vectors before transformation into prokatyotic or eukaryotic cells for replication and/or expression. The intermediate vectors are typically prokaryote vectors or shuttle vectors.

C. Expression in Prokayotes and Eukaryotes

To obtain high level expression of a cloned gene, such as those cDNAs encoding HsKip3b, it is important to construct an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the HsKip3b protein are available in, e.g., $E.$ $coli$, Bacillus sp., and Salmonella (Palva et al., $Gene$ 22:229–235 (1983); Mosbach et al., $Nature$ 302:543–545 (1983). Kits for such expression systems are commercially available. Eukaryotic expression systems for mammalian cells, yeast, and insect cells are well known in the art and are also commercially available. The pET expression system (Novagen) is a preferred prokaryotic expression system.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the HsKip3b encoding nucleic acid in host cells. A typical expression cassette thus contains a promoter operably linked to the nucleic acid sequence encoding HsKip3b and signals required for efficient polyadenylation of the transcript, ribosome binding sites, and translation termination. The nucleic acid sequence encoding HsKip3b may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of $Heliothis$ $virescens$. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322based plasmids, pSKF, pET23, and fusion expression systems such as GST and LacZ. Epitope tags can also be added to recombinant proteins to provide convenient methods of isolation, e.g., c-myc or histidine tags.

Expression vectors containing regulatory elements from eukaryotic viruses are typically used in eukaryotic expression vectors, e.g., SV40 vectors, cytomegalovirus vectors, papilloma virus vectors, and vectors derived from Epstein Bar virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, CMV promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a HsKip3b encoding sequence under the direction of the polyhedrin promoter or other strong baculovirus promoters.

The elements that are typically included in expression vectors also include a replicon that functions in $E.$ $coli$, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection or transformation methods are used to produce bacterial, mammalian, yeast or insect cell lines that express large quantities of HsKip3b protein, which are then purified using standard techniques (see, e.g., Colley et al., $J.$ $Biol.$ $Chem.$ 264:17619–17622 (1989); $Guide$ $to$ $Protein$ $Purification,$ in Methods in Enzymology, vol. 182 (Deutscher ed., 1990)).

Transformation of eukaryotic and prokaryotic cells are performed according to standard techniques (see, e.g., Morrison, $J.$ $Bact.$, 132:349–351 (1977); Clark-Curtiss & Curtiss, $Methods$ $in$ $Enzymology$, 101:347–362 (Wu et al., eds, 1983). Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing HsKip3b.

After the expression vector is introduced into the cells, the transfected cells are cultured under conditions favoring expression of HsKip3b, which is recovered from the culture using standard techniques identified below.

IV. Purification of UsKip3b Protein

Either naturally occurring or recombinant HsKip3b can be purified for use in functional assays. In a preferred embodiment, the target proteins are purified for use in the assays to provide substantially pure samples. Alternatively, the target protein need not be substantially pure as long as the sample comprising the target protein is substantially free of other components that can contribute to the production of ADP or phosphate.

The target proteins may be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse phase HPLC chromatography, chromatofocussing, selective precipitation with such substances as ammonium sulfate;and others (see, e.g., Scopes, Protein Purification: Principles and Practice (1982); U.S. Pat. No. 4,673,641; Ausubel et al. supra; and Sambrook et al., supra). For example, the target protein can be purified using a standard anti-target antibody column. Ultrafiltration and diafiltration techniques, in conjunction with protein concentration, are also useful. A preferred method of purification is use of Ni-NTA agarose (Qiagen).

The expressed protein can be purified by standard chromatographic procedures to yield a purified, biochemically active protein. The activity of any of the peptides provided herein can be routinely confirmed by the assays provided herein such as those which assay ATPase activity or microtubule binding activity. Biologically active target protein is useful for identifying modulators of target protein or fragments thereof and kinesin superfamily members using in vitro assays such as microtubule gliding assays, ATPase assays (Kodama et al., J. Biochem. 99:1465–1472 (1986); Stewart et al., Proc. Nat'l Acad. Sci. USA 90:5209–5213 (1993)), and binding assays including microtubule binding assays (Vale et al., Cell 42:39–50 (1985)), as described in detail below.

A. Purification of HsKip3b from Recombinant Bacteria

Recombinant proteins are expressed by transformed bacteria in large amounts, typically after promoter induction; but expression can be constitutive. Promoter induction with IPTG is a preferred method of expression. Bacteria are grown according to standard procedures in the art. Fresh or frozen bacteria cells are used for isolation of protein. Alternatively, it is possible to purify HsKip3b from bacteria periplasm. After HsKip3b is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Suitable purification schemes for some specific kinesins are outlined in U.S. Ser. No. 09/295,612, filed Apr. 20, 1999, hereby expressly incorporated herein in its entirety for all purposes.

B. Standard Protein Separation Techniques For Purifying HsKip3b

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of HsKip3b can be used to isolated it from proteins of greater and lesser size using ultrafiltration through membranes of different pore size (for example, Amicon or Millipore membranes). As a first step, the protein mixture is ultra filtered through a membrane with a pore size that has a lower molecular weight cut-off than the molecular weight of the protein of interest. The retentate of the ultrafiltration is then ultra filtered against a membrane with a molecular cut off greater than the molecular weight of the protein of interest. The recombinant protein will pass through the membrane into the filtrate. The filtrate can then be chromatographed as described below.

Column Chromatoeraphy

HsKip3b can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of HsKip3b

In addition to the detection of HsKip3b genes and gene expression using nucleic acid hybridization technology, one can also use immunoassays to detect HsKip3b. Immunoassays can be used to qualitatively or quantitatively analyze HsKip3b. A general overview of the applicable technology can be found in Harlow & Lane, *Antibodies: A Laboratory Manual* (1988).

A. Antibodies to HsKip3b

Methods of producing polyclonal and monoclonal antibodies that react specifically with HsKip3b are known to those of skill in the art (see, e.g., Coligan, *Current Protocols in Immunology* (1991); Harlow & Lane, sara; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of HsKip3b comprising immunogens may be used to produce antibodies specifically reactive with HsKip3b. For example, recombinant HsKip3b or a antigenic fragment thereof such as the motor domain, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to HsKip3b. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-HsKip3b proteins or even other homologous proteins from other organisms (e.g., *C. elegans* unc-104 or human Kif1A), using a competitive binding immunoassay. Specific polyclonal antisera and monoclonal antibodies will usually bind with a $K_d$ of at least about 0.1 mM, more usually at least about 1 $\mu$m, preferably at least about 0.1 $\mu$M or better, and most preferably, 0.01 $\mu$M or better.

Once HsKip3b specific antibodies are available, HsKip3b can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio ed., 1980); and Harlow & Lane, supra.

B. Binding Assays

Antibodies can be used for treatment or to identify the presence of HsKip3b having the sequence identity characteristics as described herein. Additionally, antibodies can be used to identify modulators of the interaction between the antibody and HsKip3b as further described below. While the following discussion is directed toward the use of antibodies in the use of binding assays, it is understood that the same general assay formats such as those described for "non-competitive" or "competitive" assays can be used with any compound which binds to HsKip3b such as microtubules or the compounds described in U.S. Ser. No. 60/070,772.

In a preferred embodiment, HsKip3b is detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology* Volume 37: *Antibodies in Cell Biology* (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the HsKip3b or antigenic subsequence thereof). The antibody (e.g., anti-HsKip3b) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled HsKip3b polypeptide or a labeled anti-HsKip3b antibody. Alternatively, the labeling agent may be a third moiety, such a secondary antibody, that specifically binds to the antibody/HsKip3b complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see generally Kronval et al., *J. Immunol* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 4° C. to 40° C.

Non-Competitive Assay Formats

Immunoassays for detecting HsKip3b in samples may be either competitive or noncompetitive. Noncompetitive immunoassays are assays in which the amount of antigen is directly measured. In one preferred "sandwich" assay, for example, the anti-HsKip3b antibodies can be bound directly to a solid substrate on which they are immobilized. These immobilized antibodies then capture HsKip3b present in the test sample. HsKip3b is thus immobilized is then bound by a labeling agent, such as a second HsKip3b antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of HsKip3b present in the sample is measured indirectly by measuring the amount of a known, added (exogenous) HsKip3b displaced (competed away) from an anti-HsKip3b antibody by the unknown HsKip3b present in a sample. In one competitive assay, a known amount of HsKip3b is added to a sample and the sample is then contacted with an antibody that specifically binds to HsKip3b. The amount of exogenous HsKip3b bound to the antibody is inversely proportional to the concentration of HsKip3b present in the sample. In a particularly preferred embodiment, the antibody is immobilized on a solid substrate. The amount of HsKip3b bound to the antibody may be determined either by measuring the amount of HsKip3b present in a HsKip3b/antibody complex, or alternatively by measuring the amount of remaining uncomplexed protein. The amount of HsKip3b may be detected by providing a labeled HsKip3b molecule.

A hapten inhibition assay is another preferred competitive assay. In this assay the known HsKip3b, is immobilized on a solid substrate. A known amount of anti-HsKip3b antibody is added to the sample, and the sample is then contacted with the HsKip3b. The amount of anti-HsKip3b antibody bound to the known immobilized HsKip3b is inversely proportional to the amount of HsKip3b present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a protein at least partially encoded by SEQ ID NO:2 can be immobilized to a solid support. Proteins (e.g., *C. elegans* unc-104 or human Kif1A) are added to the assay that compete for binding of the antisera to the immobilized antigen. The ability of the added proteins to compete for binding of the antisera to the immobilized protein is compared to the ability of HsKip3b encoded by SEQ ID NO:2 to compete with itself The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologues.

The immunoabsorbed and pooled antisera are then used in a competitive binding immunoassay as described above to compare a second protein, thought to be perhaps the protein of this invention, to the immunogen protein (i.e., HsKip3b of SEQ ID NO:2). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2 that is required to inhibit 50% of binding, then the second protein is said to specifically bind to the polyclonal antibodies generated to a HsKip3b immunogen.

Other Assay Formats

Western blot (immunoblot) analysis is used to detect and quantify the presence of HsKip3b in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind HsKip3b. The anti-HsKip3b antibodies specifically bind to the HsKip3b on the solid support. These antibodies may be directly labeled or alternatively may be subsequently detected using labeled antibodies (e.g., labeled sheep anti-mouse antibodies) that specifically bind to the anti-HsKip3b antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the ii field of immunoassays and, in general, most any label usefull in such methods can be applied to the present invention. Thus, a label is any composition detectable by spectroscopic, photochemical, biochemical, immunochemical, electrical, optical or chemical means.

Useful labels in the present invention include magnetic beads (e.g., DYNABEADSTM), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), colorimetric labels such as colloidal gold or colored glass or plastic beads (e.g., polystyrene, polypropylene, latex, etc.) or other labels that can be detected by mass spectroscopy, NMR spectroscopy, or other analytical means known in the art.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize HsKip3b, or secondary antibodies that recognize anti-HsKip3b.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodarnine and its derivatives, dansyl, urnbelliferone, etc. Chemiluminescent compounds include luciferin, and 2,3-dihydrophthalazinediones, e.g., luminol. For a review of various labeling or signal producing systems which may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of the Target Protein

A. Functional Assays

Assays that can be used to test for modulators of the target protein include a variety of in vitro or in vivo assays, e.g., microtubule gliding assays, binding assays such as microtubule binding assays, microtubule depolymerization assays, and ATPase assays (Kodama et al., J. Biochem. 99: 1465–1472 (1986); Stewart et al., Proc. Nat'l Acad. Sci. USA 90:5209–5213 (1993); (Lombillo et al., J. Cell Biol. 128:107–115 (1995); (Vale et al., Cell 42:39–50 (1985)).

Modulation is tested by screening for candidate agents capable of modulating the activity of the target protein comprising the steps of combining a candidate agent with the target protein, as above, and determining an alteration in the biological activity of the target protein. Thus, in this embodiment, the candidate agent should both bind to the target protein (although this may not be necessary), and alter its biological or biochemical activity as defined herein. The methods include both in vitro screening methods and in vivo screening of cells for alterations in cell cycle distribution, cell viability, or for the presence, morphology, activity, distribution, or amount of mitotic spindles, as are generally outlined above.

In a preferred embodiment, molecular motor activity is measured by the methods disclosed in U.S. Ser. No. 09/314,464, filed May 18, 1999, entitled "Compositions and assay utilizing ADP or phosphate for detecting protein modulators", which is incorporated herein by reference in its entirety. More specifically, this assay detects modulators of any aspect of a kinesin motor function ranging from interaction with microtubules to hydrolysis of ATP. ADP or phosphate is used as the readout for protein activity.

There are a number of enzymatic assays known in the art which use ADP as a substrate. For example, kinase reactions such as pyruvate kinases are known. See, Nature 78:632 (1956) and Mol. Pharmacol. 6:31 (1970). This is a preferred method in that it allows the regeneration of ATP. In one embodiment, the level of activity of the enzymatic reaction is determined directly. In a preferred embodiment, the level of activity of the enzymatic reaction which uses ADP as a substrate is measured indirectly by being coupled to another reaction. For example, in one embodiment, the method further comprises a lactate dehydrogenase reaction under conditions which normally allow the oxidation of NADH, wherein said lactate dehydrogenase reaction is dependent on the pyruvate kinase reaction. Measurement of enzymatic reactions by coupling is known in the art. Furthermore, there are a number of reactions which utilize phosphate. Examples of such reactions include a purine nucleoside phosphorylase reaction. This reaction can be measured directly or indirectly. A particularly preferred embodiments utilizes the pyruvate kinase/lactate dehydrogenase system.

In one embodiment, the detection of the ADP or phosphate proceeds non-enzymatically, for example, by binding or reacting the ADP or phosphate with a detectable compound. For example, phosphomolybdate based assays may be used which involve conversion of free phosphate to a phosphomolybdate complex. One method of quantifying the phosphomolybdate is with malachite green. Alternatively, a fluorescently labeled form of a phosphate binding protein, such as the *E. coli* phosphate binding protein, can be used to measure phosphate by a shift in its fluorescence.

In addition, target protein activity can be examined by determining modulation of target protein in vitro using cultured cells. The cells are treated with a candidate agent and the effect of such agent on the cells is then determined either directly or by examining relevant surrogate markers. For example, characteristics such as mitotic spindle morphology and cell cycle distribution can be used to determine the effect.

Thus, in a preferred embodiment, the methods comprise combining a target protein and a candidate agent, and determining the effect of the candidate agent on the target protein. Generally a plurality of assay mixtures are run in parallel with different agent concentrations to obtain a differential response to the various concentrations. Typically, one of these concentrations serves as a negative control, i.e., at zero concentration or below the level of detection.

As will be appreciated by those in the art, the components may be added in buffers and reagents to assay target protein activity and give optimal signals. Since the methods allow kinetic measurements, the incubation periods can be optimized to give adequate detection signals over the background.

In a preferred embodiment, an antifoam or a surfactant is included in the assay mixture. Suitable antifoams include, but are not limited to, antifoam 289 (Sigrna). Suitable surfactants include, but are not limited to, Tween, Tritons, including Triton X-100, saponins, and polyoxyethylene ethers. Generally, the antifoams, detergents, or surfactants are added at a range from about 0.01 ppm to about 10 ppm.

A preferred assay design is also provided. In one aspect, the invention provides a multi-time-point (kinetic) assay, with at least two data points being preferred. In the case of multiple measurements, the absolute rate of the protein activity can be determined.

B. Binding Assays

In a preferred embodiment, the binding of the candidate agent is determined through the use of competitive binding assays. In this embodiment, the competitor is a binding moiety known to bind to the target protein, such as an antibody, peptide, binding partner, ligand, etc. Under certain circumstances, there may be competitive binding as between the candidate agent and the binding moiety, with the binding moiety displacing the candidate agent.

Competitive screening assays may be done by combining the target protein and a drug candidate in a first sample. A second sample comprises a candidate agent, the target protein and a compound that is known to modulate the target protein. This may be performed in either the presence or absence of microtubules. The binding of the candidate agent is determined for both samples, and a change, or difference in binding between the two samples indicates the presence of an agent capable of binding to the target protein and potentially modulating its activity. That is, if the binding of the candidate agent is different in the second sample relative to the first sample, the candidate agent is capable of binding to the target protein.

In one embodiment, the candidate agent is labeled. Either the candidate agent, or the competitor, or both, is added first to the target protein for a time sufficient to allow binding. Incubations may be performed at any temperature which facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to the target protein and thus is capable of binding to, and potentially modulating, the activity of the target protein. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to the target protein with a higher affinity. Thus, if the candidate agent is labeled, the presence of the label on the support, coupled with a lack of competitor binding, may indicate the candidate agent is capable of binding to the target protein.

C. Candidate Agents

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. In a preferred embodiment, the candidate agents are organic chemical moieties, a wide variety of which are available in the literature.

D. Other Assay Components

The assays provided utilize target protein as defined herein. In one embodiment, portions of target protein are utilized; in a preferred embodiment, portions having target protein activity as described herein are used. In addition, the assays described herein may utilize either isolated target proteins or cells or animal models comprising the target proteins.

A variety of other reagents may be included in the screening assays. These include reagents like salts, neutral proteins, e.g. albumin, detergents, etc which may be used to facilitate optimal protein-protein binding and/or reduce non-specific or background interactions. Also, reagents that otherwise improve the efficiency of the assay, such as protease inhibitors, nuclease inhibitors, anti-microbial agents, etc., may be used. The mixture of components may be added in any order that provides for the requisite binding.

VII. Applications

The methods of the invention are used to identify compounds useful in the treatment of cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals afflicted or impending affliction with any one of these disorders or states.

The compositions and methods provided herein are particularly deemed useful for the treatment of cancer including solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesotheliorna; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinorna, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfiroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinorna, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematolopic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

Accordingly, the compositions of the invention are administered to cells. By "administered" herein is meant administration of a therapeutically effective dose of the candidate agents of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant alnost any cell in which mitosis or meiosis can be altered.

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

Candidate agents having the desired pharmacological activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1–100 wt.%. The agents maybe administered alone or in combination with other treatments, i.e., radiation, or other chemotherapeutic agents.

In a preferred embodiment, the pharmaceutical compositions are in a water soluble form, such as pharmaceutically acceptable salts, which is meant to include both acid and base addition salts.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The administration of the candidate agents of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the candidate agents may be directly applied as a solution or spray.

One of skill in the art will readily appreciate that the methods described herein also can be used for diagnostic applications. A diagnostic as used herein is a compound or method that assists in the identification and characterization of a health or disease state in humans or other animals.

The present invention also provides for kits for screening for modulators of the target protein. Such kits can be prepared from readily available materials and reagents. For example, such kits can comprise any one or more of the following materials: biologically active target protein, reaction tubes, and instructions for testing activity of the target protein. Preferably, the kit contains biologically active target protein. A wide variety of kits and components can be prepared according to the present invention, depending upon the intended user of the kit and the particular needs of the user. For example, the kit can be tailored for ATPase assays, microtubule gliding assays, or microtubule binding assays.

VIII. Examples

This assay is based on detection of ADP production from a target protein's microtubule stimulated ATPase. ATP production is monitored by a coupled enzyme system consisting of pyruvate kinase and lactate dehydrogenase. Under the assay conditions described below, pyruvate kianse catalyzes the conversion of ADP and phosphoenol pyruvate to pyruvate and ATP. Lactate dehydrogenase then catalyzes the oxidationreduction reaction of pyruvate and NADH to lactate and NAD+. Thus, for each molecule of ADP produced, one molecule of NADH is consumed. The amount of NADH in the assay solution is monitored by measuring light absorbance at a wavelength of 340 nm.

The final 25 µl assay solution consists of the following:5 µg/ml target protein, 30 µg/ml microtubules, 5 µM Taxol, 0.8 mM NADH, 1.5 mM phosphoenol pyruvate, 3.5 U/ml pyruvate kinase, 5 U/ml lactate dehydrogenase, 25 mM Pipes/KOH pH 6.8, 2 mM $MgCl_2$, 1 mM EGTA, 1 mM MDTT, 0.1 mg/ml BSA, 0.001% antifoam 289, and 1 mM ATP.

Potential candidate agents are dissolved in DMSO at a concentration of about 1 mg/ml and 0.5 µl of each chemical solution is dispensed into a single well of a clear 384 well plate. Each of the 384 wells are then filled with 20 µl of a solution consisting of all of the assay components described above except for ATP. The plate is agitated at a high frequency. To start the assay,5 µl of a solution containing ATP is added to each well. The plate is agitated and the absorbance is read at 340 nm over various time intervals. The assay is run at room temperature.

The assay components and the performance of the assay are optimized together to match the overall read time with the rate of the target protein's ADP production. The read time should be long enough for the rate of NADH consumption to reach steady state beyond an initial lag time of several seconds.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

What is claimed is:

1. An isolated nucleic acid sequence encoding a microtubule motor protein, wherein the motor protein has the following properties: (i) the protein's activity includes microtubule stimulated ATPase activity; and (ii) the protein has a sequence that has greater than 70% amino acid sequence identity to SEQ ID NO:2 as measured using a sequence comparison algorithm.

2. An isolated nucleic acid sequence of claim 1, wherein the protein specifically binds to polyclonal antibodies to a protein comprising SEQ ID NO:2.

3. An isolated nucleic acid sequence of claim 1, wherein the nucleic acid encodes SEQ ID NO:2.

4. An isolated nucleic acid sequence of claim 1, wherein the nucleic acid has a nucleotide sequence of SEQ ID NO:1.

5. An expression vector comprising a nucleic acid encoding a microtubule motor protein, wherein the motor protein has the following properties: (i) the protein's activity includes microtubule stimulated ATPase activity; and (ii) the protein has a sequence that has greater than 70% amino acid sequence identity to SEQ ID NO:2 as measured using a sequence comparison algorithm.

6. A host cell transfected with the vector of claim 6.

* * * * *

SEQUENCE LISTING

<160> NUMBER OF SEQ ID NOS: 2

<210> SEQ ID NO 1
<211> LENGTH: 897
<212> TYPE: DNA
<213> ORGANISM: Human
<220> FEATURE:
<221> NAME/KEY: misc_feature
<222> LOCATION: (472)...(495)
<223> OTHER INFORMATION: n = a, c, t, or g

<400> SEQUENCE: 1

```
gtgaccgtgg gcctccctct ggggaccttg cagatggtgg ttctcatgga cccaatggag      60
gatcccgacg acatcctgcg ggcgcatcgc tcccgggaga agtcctacct gttcgacgtg     120
gcctttgact tcaccgccac ccaggagatg gtgtatcagg ccaccaccaa gagcctcatc     180
gagggcgtca tctcaggcta caatgccact gtctttgcct atggcccac aggctgtggg      240 aaaacctaca ccatgctggg cacagaccag gagcctggca tctatgttca gaccctcaac     300
gacctcttcc gtgccatcga ggagaccagc aatgacatga gtatgaggt ctccatgtcc      360 tacctggaga tctacaatga gatgatccgg gacctgctga accctccct gggctacctg      420 gagctgcggg aggactctaa gggggtgatc caggtggccg gcatcaccga annnnnnnn      480 nnnnnnnnnn nnnnnatcat gcagctgctg atgaagggga accggcagag gacccaggag    540
cccacggccg ccaaccagac gtcctcccgc tcccacgcgg gccgcctgtt catgatcgac    600
ctggctggct cagagcgcgc ctcgcagaca cagaatcgtg ggcagcgtat gaaggagggg    660
gcccacatca accgctcact gctggcactg ggcaactgca tcaacgccct gagcgacaag    720
```

```
ggtagcaaca agtacatcaa ctatcgcgac agcaagctca cccggctcct gaaggactct      780
ctgggaggaa acagccgcac agtgatgatc gctcacatca gtcctgcgag cagtgccttc      840
gaggagtccc ggaacaccct gacctacgcc ggccgggcca agaacattaa gactagg         897
```

<210> SEQ ID NO 2
<211> LENGTH: 299
<212> TYPE: PRT
<213> ORGANISM: Human
<220> FEATURE:
<221> NAME/KEY: VARIANT
<222> LOCATION: (158)...(165)
<223> OTHER INFORMATION: Xaa = any amino acid

<400> SEQUENCE: 2

```
Val Thr Val Gly Leu Pro Leu Gly Thr Leu Gln Met Val Val Leu Met
 1               5                  10                  15

Asp Pro Met Glu Asp Pro Asp Asp Ile Leu Arg Ala His Arg Ser Arg
            20                  25                  30

Glu Lys Ser Tyr Leu Phe Asp Val Ala Phe Asp Phe Thr Ala Thr Gln
        35                  40                  45

Glu Met Val Tyr Gln Ala Thr Thr Lys Ser Leu Ile Glu Gly Val Ile
    50                  55                  60

Ser Gly Tyr Asn Ala Thr Val Phe Ala Tyr Gly Pro Thr Gly Cys Gly
65                  70                  75                  80

Lys Thr Tyr Thr Met Leu Gly Thr Asp Gln Glu Pro Gly Ile Tyr Val
                85                  90                  95

Gln Thr Leu Asn Asp Leu Phe Arg Ala Ile Glu Glu Thr Ser Asn Asp
            100                 105                 110

Met Glu Tyr Glu Val Ser Met Ser Tyr Leu Glu Ile Tyr Asn Glu Met
        115                 120                 125

Ile Arg Asp Leu Leu Asn Pro Ser Leu Gly Tyr Leu Glu Leu Arg Glu
    130                 135                 140

Asp Ser Lys Gly Val Ile Gln Val Ala Gly Ile Thr Glu Xaa Xaa Xaa
145                 150                 155                 160

Xaa Xaa Xaa Xaa Xaa Ile Met Gln Leu Leu Met Lys Gly Asn Arg Gln
                165                 170                 175

Arg Thr Gln Glu Pro Thr Ala Ala Asn Gln Thr Ser Ser Arg Ser His
            180                 185                 190

Ala Gly Arg Leu Phe Met Ile Asp Leu Ala Gly Ser Glu Arg Ala Ser
        195                 200                 205

Gln Thr Gln Asn Arg Gly Gln Arg Met Lys Glu Gly Ala His Ile Asn
    210                 215                 220

Arg Ser Leu Leu Ala Leu Gly Asn Cys Ile Asn Ala Leu Ser Asp Lys
225                 230                 235                 240

Gly Ser Asn Lys Tyr Ile Asn Tyr Arg Asp Ser Lys Leu Thr Arg Leu
                245                 250                 255

Leu Lys Asp Ser Leu Gly Gly Asn Ser Arg Thr Val Met Ile Ala His
            260                 265                 270

Ile Ser Pro Ala Ser Ser Ala Phe Glu Glu Ser Arg Asn Thr Leu Thr
        275                 280                 285

Tyr Ala Gly Arg Ala Lys Asn Ile Lys Thr Arg
    290                 295
```